United States Patent

Chan et al.

[11] Patent Number: 5,993,473
[45] Date of Patent: Nov. 30, 1999

[54] EXPANDABLE BODY DEVICE FOR THE GASTRIC CAVITY AND METHOD

[76] Inventors: Yung C. Chan; Mei H. Chan, both of 101 1st St., NW., Pulaski, Va. 24301

[21] Appl. No.: 08/972,965

[22] Filed: Nov. 19, 1997

[51] Int. Cl.⁶ .................................................. A61M 29/00
[52] U.S. Cl. .......................... 606/192; 606/191; 606/159; 604/96
[58] Field of Search ..................................... 606/192, 159, 606/191, 193–198; 128/897; 604/96

[56] References Cited

U.S. PATENT DOCUMENTS

| | | | |
|---|---|---|---|
| 1,282,881 | 10/1918 | Landis | 606/192 |
| 1,690,995 | 11/1928 | Pratt | 606/192 |
| 4,133,315 | 1/1979 | Berman et al. | 128/344 |
| 4,246,893 | 1/1981 | Berson | 128/1 |
| 4,416,267 | 11/1983 | Garren et al. | 128/1 |
| 4,607,618 | 8/1986 | Angelchick | 128/1 |
| 4,648,383 | 3/1987 | Angelchik | 128/1 |
| 4,694,827 | 9/1987 | Weiner et al. | 128/303 |
| 4,723,547 | 2/1988 | Kullas et al. | 128/329 |
| 4,762,130 | 8/1988 | Forgarty | 606/159 |
| 4,823,808 | 4/1989 | Clegg et al. | 128/773 |
| 4,899,747 | 2/1990 | Garren et al. | 606/192 |
| 5,234,454 | 8/1993 | Bangs | 606/191 |
| 5,259,399 | 11/1993 | Brown | 128/897 |
| 5,327,914 | 7/1994 | Shlain | 128/898 |
| 5,340,315 | 8/1994 | Kaye | 434/127 |

FOREIGN PATENT DOCUMENTS

WO 9309722  5/1993  WIPO .................................... 606/192

*Primary Examiner*—Michael Buiz
*Assistant Examiner*—Lien Ngo
*Attorney, Agent, or Firm*—Klima & Pezzlo, P.C.

[57] ABSTRACT

An expandable body device for the gastric cavity including an elastic expandable body, a rigid fillant delivery tube sealedly connected to the expandable body and having a base portion, an extending portion, and a tip portion. An anchor and a valve are included on the base portion of the fillant delivery tube. A method of treating obesity including the steps of performing a percutaneous endoscopic gastrostomy to establish a gastro-cutaneous fistula, pushing an expandable body through said fistula into the gastric cavity with a rigid fillant delivery tube to which the expandable body is sealedly connected, the rigid fillant delivery tube including a base portion, an extending portion, a tip portion, and an anchor attached to the base portion, delivering a fillant through a valve connected to the fillant delivery tube such that the fillant flows into the fillant delivery tube and the expandable body to cause the expandable body to expand within the gastric cavity, delivering the fillant through the valve out of the fillant delivery tube and the expandable body to cause the expandable body to return to a non-expanded configuration, and removing the fillant delivery tube and the expandable body from the fistula.

17 Claims, 6 Drawing Sheets

EXPANDABLE BODY DEVICE FOR THE GASTRIC CAVITY AND METHOD

FIELD OF THE INVENTION

This invention is directed to an expandable body device for the gastric cavity and method, particularly, for the treatment of obesity.

BACKGROUND OF THE INVENTION

Obesity is a major health problem for many individuals. Many solutions for achieving the weight loss necessary to treat this problem have been proposed.

Common to many of these solutions is the requirement of the obese individual to decrease overall caloric intake and/or to increase energy output. One solution for reducing caloric intake may involve instructing the obese individual to consume foods which have a relatively low calorie to volume ratio, for example, low fat foods. Typically, however, this solution, by itself, is not sufficient for many overweight individuals because of an inability to select such foods for consumption. Oftentimes this is due to a lack of knowledge about nutrition and/or a lack of self-control.

In many cases vigorous exercise is recommended to achieve an increase in energy output. However, many overweight individuals, particularly, the morbidly obese, risk further damage to their health, for example, heart attacks, from such activity.

Other solutions involve the use of pharmaceuticals, for example, stimulative or appetite suppressive drugs. While this may be a satisfactory solution for many, the use of pharmaceuticals in the treatment of obesity is not without drawbacks. For example, individuals using such drugs are at risk of becoming addicted or ill-affected by side effects of the drugs. Further, these drugs oftentimes become less potent over time due to the development of a high drug tolerance.

Surgical solutions to the problem of obesity have also been proposed. Some of these procedures involve reducing the volume of the gastric cavity, for example, by creating a small pouch gastric bypass, or reducing the capacity of the stomach to expand, for example, by placing a constrictive band around the stomach. These surgical procedures are particularly traumatic to the body and are thus often associated with serious complications and increased mortality rates.

Thus, there continues to be a need for effective solutions to the problem of obesity.

Accordingly, it is first object of the present invention to provide an expandable body device for the gastric cavity and method.

It is a second object of the present invention to provide an improved expandable body device for the gastric cavity and method.

It is a third object of the present invention to provide an expandable body device for the gastric cavity and method of treating obesity.

It is a fourth object of the present invention to provide an expandable body device for the gastric cavity which is easily introduced to and removed from the gastric cavity.

It is a fifth object of the present invention to provide an expandable body device for the gastric cavity which may be introduced to and removed from the gastric cavity through a gastro-cutaneous fistula having a transverse cross-sectional profile which defines a relatively small area.

It is a sixth object of the present invention to provide an expandable body device for the gastric cavity which minimally contacts the inner surface of the gastric wall.

It is a seventh object of the present invention to provide an expandable body device for the gastric cavity which is prevented from moving relative to the individual in whose gastric cavity the device has been introduced.

It is an eighth object of the present invention to provide an expandable body device for the gastric cavity which includes an expandable body which is prevented from excessive movement while in the gastric cavity.

It is a ninth object of the present invention to provide an expandable body device for the gastric cavity which is comfortable for the person in whose gastric cavity the device has been introduced.

It is a tenth object of the present invention to provide an expandable body device for the gastric cavity which does not allow for gastric juices to escape from the gastric cavity.

It is an eleventh object of the present invention to provide an expandable body device for the gastric cavity which includes a minimum number of parts.

It is a twelfth object of the present invention to provide an expandable body device for the gastric cavity which is inconspicuous while in use.

It is a thirteenth object of the present invention to provide an expandable body device for the gastric cavity which is easy to manufacture.

It is a fourteenth object of the present invention to provide an expandable body device for the gastric cavity which is safe to use.

It is a fifteenth object of the present invention to provide an expandable body device for the gastric cavity which includes a small number of parts.

The present invention provides an expandable body device for the gastric cavity and method. The preferred embodiment of the present invention includes a rigid to semi-rigid fillant delivery tube having a base portion, an extending portion, and a tip portion. The fillant delivery tube is sealedly connected to an expandable body which is preferably constructed of surgical grade latex rubber. In a preferred embodiment, the extending portion and tip portion of the fillant delivery tube extend into the expandable body, which forms a substantially proximal and uniformly congruent layer thereover. An anchor and a valve are provided on the base portion of the fillant delivery tube.

To use a device constructed according to a preferred embodiment of the present invention for the treatment of obesity, a gastro-cutaneous fistula is established in the obese individual via a percutaneous endoscopic gastrostomy, a procedure well known to persons skilled in the art. The cross-sectional profile of the fistula tract is configured to correspond with the cross-sectional profile of the device along the expandable body.

Preferably, the fistula tract is allowed to mature (i.e. form scar tissue) over a period of from 1–2 weeks. Then, the device is brought into proximity of the fistula tract and a bio-compatible lubricant is applied to the device and/or to the fistula tract. The tip portion of the fillant delivery tube and the expandable body are placed at the entrance of the fistula tract and passed through the fistula by the application of a gentle force at the base portion of the fillant delivery tube. The anchor provides a convenient surface against which such a force may be applied.

The device is fully inserted when the anchor contacts the abdominal wall. The expandable body may then be expanded with a biocompatible fillant. A graduated syringe is loaded with an appropriate amount, typically 100–500 ml, of saline solution. The syringe is then sealedly engaged with the valve on the proximal end of the fillant delivery tube and the fillant is forced into the fillant delivery tube by depressing the syringe plunger, thereby causing the expandable body to expand within the gastric cavity. Once appropriate expansion size is reached, the tip of the syringe is removed from the valve which is preferably configured to seal upon withdrawal of the syringe.

The size of the of the expandable body is preferably configured so that when appropriate expansion size is reached, the expandable body occupies a substantial fraction of the total volume of the gastric cavity of the person in whose gastric cavity the device is introduced. This enables the individual to feel satiated or "full" after consuming a relatively small portion of food.

After a period of time, preferably 3 to 6 months, the syringe is again engaged with the valve. The plunger of the syringe is operated to create a vacuum condition in the syringe cylinder, thereby causing fillant to flow from the device into the syringe until the expandable body is returned to a non-expanded configuration. Once the expandable body is returned to a non-expanded configuration, the device may be re-filled, for example, to a new volume, or easily removed from the gastric cavity by simply pulling on the base portion of the flilant delivery tube.

Alternatively, a hose may be connected between a fillant supply pump and a valve on the fillant delivery tube. The valve is opened and a biocompatible fillant, for example, air or saline, is pumped through the valve and into the fillant delivery tube. The fillant goes through the fillant delivery tube and enters the expandable body causing the expandable body to expand within the gastric cavity. After a period of time, the hose is again connected to the valve. Upon opening of the valve, the force of the elastic expandable body forces fillant from the expandable body into the fillant delivery tube and out of the device. Thereafter, the device may be re-filled with fillant or easily removed from the gastric cavity by simply pulling on the base portion of the fillant delivery tube.

While the function of the present invention to provide a deterrent to the consumption of food is easily appreciated, it is important to realize that the present invention allows this benefit to be realized with a lower risk of health problems, smaller loss of healthy social activity, and lower monetary cost than known methods of treating obesity.

To begin, the fillant delivery tube is preferably provided with a tapering, closed tip portion having a rounded distal end which is easily placed at the opening of the fistula by sliding the tip portion along the abdomen until the rounded distal end engages the entrance of the fistula tract. During insertion, the tip portion gently and gradually forces open the fistula to accommodate the fillant delivery tube.

Second, the rigid to semi-rigid fillant delivery tube preferably has a circular transverse cross-sectional profile and the ratio of the longitudinal length of the tube to the diameter thereof is relatively large. Thus, the is device easily translated through the fistula tract.

Third, the tip portion and the extending portion of the fillant delivery tube are covered by the expandable body which forms a single layer of material thereover. During insertion, the tissue of the fistula contacts only the relatively soft material of the expandable body. The device may be passed through a fistula tract having a transverse cross-sectional profile only slightly larger than the transverse cross-sectional profile of the device distal of the anchor.

Further, the expandable body expands within the gastric cavity such that contact with the gastric wall or lining is minimized (i.e. a space is maintained between substantially all surfaces of the expanded expandable body and the gastric wall). Since a tip portion of the fillant delivery tube is proximal to the internal surface of the spherically shaped expandable body, if the expandable body pivots slightly, it will contact the tip portion. Since these features prevent the expandable body from contacting the gastric wall and causing for example, ulcers, the device may be maintained in an expanded configuration within the gastric cavity for extended periods of time, preferably, three (3) to six (6) months.

The distance between the proximal surface of the expandable body and the distal surface of the anchor is preferably slightly smaller than the distance between the gastric entrance of the fistula tract and the surface of the abdomen proximal to the abdominal entrance of the fistula tract. Thus, as the expandable body expands, the proximal portion of the expandable body contacts the gastric entrance of the fistula tract which causes the anchor on the fillant delivery tube to which the expandable body is sealedly connected to abut the abdominal surface proximal to the fistula entrance. The associated compressive force causes the expandable body to sealingly contact the gastric entrance of the fistula tract, thus preventing the escape of gastric juices from the gastric cavity. The force also fixates the device relative to the individual in whose gastric cavity the device has been inserted. Thus, the present invention allows a morbidly obese person to remain active during treatment involving use of the present invention without fear of gastric juices leaking from the fistula tract or discomfort which could have been caused by shifting of the device.

Moreover, when the device of the present invention is inserted in the gastric cavity, the preferably disk shaped anchor mounted on the fillant delivery tube lies substantially flush with the surface of the abdomen and the base portion of the delivery tube and the valve mounted thereon protrudes only minimally, preferably, less than three (3) centimeters. The present invention is thus inconspicuous during use.

A device according to the present invention is also easy to manufacture. For example, an expandable body may be placed over a rigid to semi-rigid fillant delivery tube in a first manufacturing step. In a second manufacturing step, an integral anchor and valve component may be press-fit onto the proximal end of the fillant delivery tube to sealedly connect the fillant delivery tube to the expandable body and to mount the anchor and valve component to the proximal end of the fillant delivery tube.

Thus, the present invention provides a device which may be easily inserted into the gastric cavity through a gastro-cutaneous fistula having a relatively small transverse cross sectional profile. Further, an individual in whose gastric cavity the device has been introduced may remain active while the device is within the gastric cavity since the device prevents leakage of gastric juices from the fistula tract and otherwise does not present a threat of injury or discomfort to the individual. Use of a device according to the present invention also facilitates social activity since it is relatively inconspicuous while inserted in the gastric cavity. Moreover, since the fillant delivery tube inhibits the expandable body of the device from contacting the gastric wall, the expandable body may be maintained in an expanded configuration, within the gastric cavity for extended periods of time. Still further, the device of the present invention may be easily manufactured in, for example, as little as two steps. Thus, the present invention provides an expandable body device and method which are particularly useful in the treatment of obesity.

DETAILED DESCRIPTION OF THE PREFERRED EMBODIMENTS

The present invention is directed to a device for insertion into the gastric cavity, and more particularly, to a device for insertion into the gastric cavity for the treatment of obesity.

Figure 1:
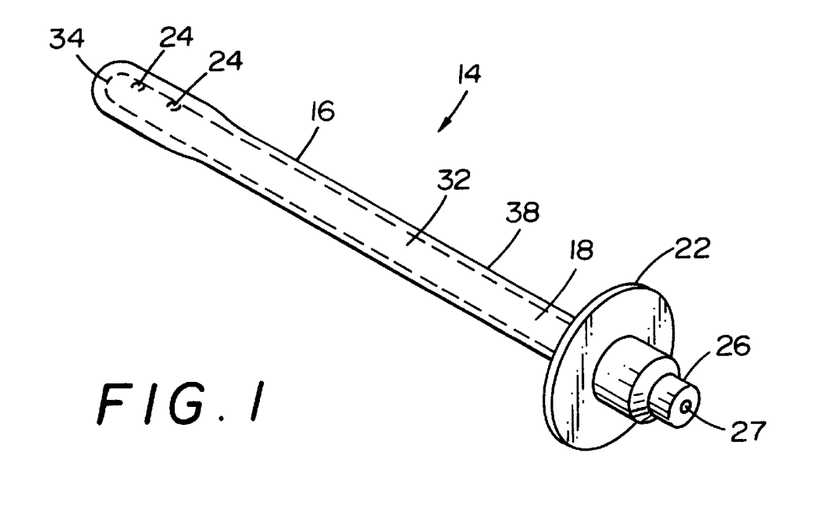
FIG. 1 shows a perspective view of a preferred embodiment of an expandable body device for the gastric cavity according to the present invention.
Figure 2:
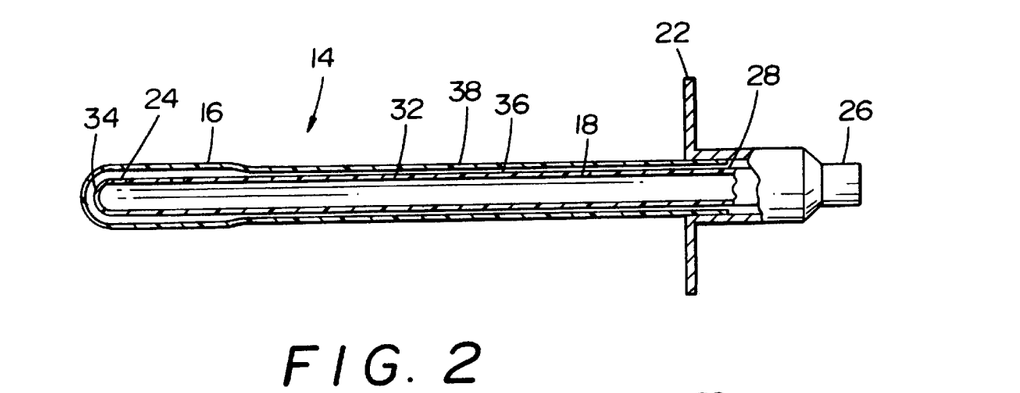
FIG. 2 shows a longitudinal partial cross-sectional view of the expandable body device shown in FIG. 1.
Figure 3:
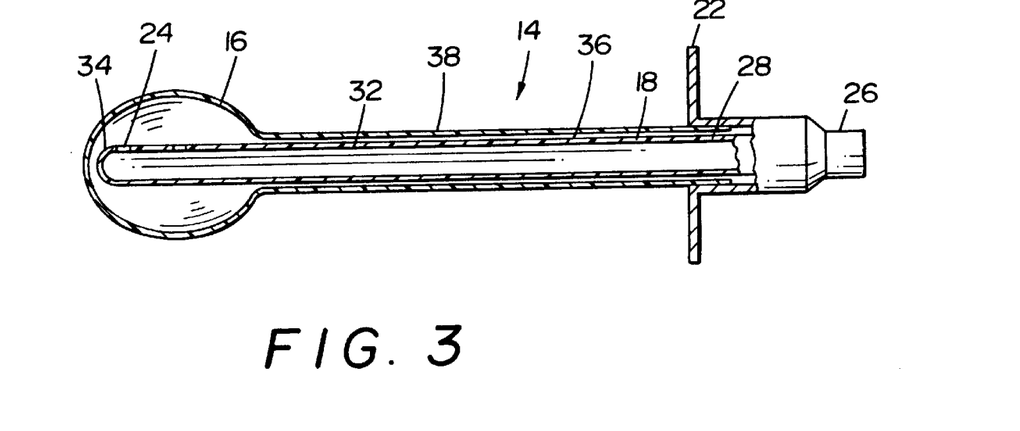
FIG. 3 shows a longitudinal partial cross-sectional view of the expandable body device shown in FIG. 1 while the expandable body is in a partially expanded configuration.

A preferred embodiment of a device 14 according to the present invention is shown in FIGS. 1–3. The device 14 includes generally, an expandable body 16 having an integral band portion 38 sealedly connected to a rigid fillant delivery tube 18 such that an extending portion 32 and a tip portion 34 of the fillant delivery tube 18 extend into the expandable body 16. A valve 26 for controlling the flow of a fillant which is delivered into and from the expandable body 16 via the fillant delivery tube 18 and an anchor 22, integral with valve 26, are connected to a base portion 28 of fillant delivery tube 18. A fillant introduced to the fillant delivery tube 18 through port 27 in valve 26 passes through passages 24 in tip portion 34 to expand the expandable body 16 as shown in FIG. 3.

The fillant delivery tube 18 shown in FIGS. 1–3 is a cylindrical and rigid tube having a linear centerline and a uniform cross-section. Fillant delivery tube is typically 6.0 to 12.0 cm in length and 0.75 to 2.0 cm in diameter. Fillant delivery tube 18 may be constructed of a metal, for example, surgical grade stainless steel, or a plastic, for example, polyethylene or polysulfone. Other materials may also be suitable of fillant delivery tube 18, for example, a semi-rigid fillant delivery tube may be constructed of silastic.

The integral anchor 22 and valve 26 of device 14 includes a circular flange portion forming anchor 22, a proximally extending first cylindrical portion which is configured to mount, for example, by a press-fit, to the base portion 28 of the fillant delivery tube 18 and a proximally extending second cylindrical portion which houses valve 26. Second cylindrical portion includes a port 27 for introducing fillant through valve 26 to fillant delivery tube 18. Valve 26 is preferably constructed of an appropriately sized cylindrical section of rubber pressed into the second cylindrical portion. The rubber section is preferably configured to automatically seal after being pierced by a small diameter cannula, for example, a syringe needle, thereby preventing the passage of fillant out of device 14.

In the preferred embodiment shown in FIGS. 1–3, tip portion 34 and extending portion 32 of fillant delivery tube 18 extend into expandable body 16 which is sealedly connected by adhesive along integral band portion 38 to fillant delivery tube 18 to form a sealed connection 36. Note that the first cylindrical portion of integral anchor 22 and valve 26 is press-fit to fillant delivery tube 18 with a portion of integral band portion 38 therebetween to further secure and sealedly connect expandable body 16 to fillant delivery tube 18.

The tip portion 34 of the preferred fillant delivery tube 18 shown in FIG. 1 is closed and rounded and has two (2) pairs of diametrically opposed passages 24 through which a fillant is delivered to the expandable body 16. The edges of passages 24 are preferably chamfered to prevent damage to the expandable body 16 during contact of fillant delivery tube 18 therewith.

In FIGS. 1–2, the expandable body 16 of device 14 is shown in a substantially non-expanded configuration. While in a non-expanded configuration, expandable body 16 conforms to and forms a single layer of material substantially congruent with the surface of fillant delivery tube 18. Expandable body 16 is preferably made of surgical grade latex rubber and is configured to expand into a substantially spherical shape having a volume of 10–500 ml upon the introduction of a bio-compatible fillant thereto. Expandable body 16 is also preferably configured to return to its original shape upon removal of fillant therefrom. Note that FIG. 3 shows the expandable body 16 of device 14 in only a partially expanded spherical configuration.

Figure 4:
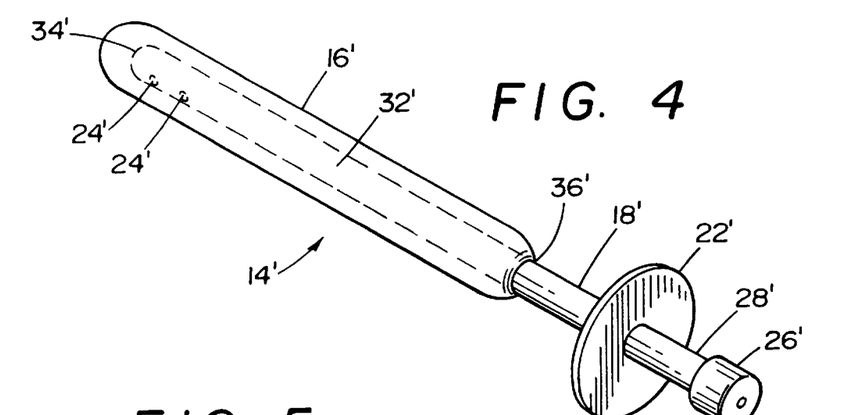
FIG. 4 shows a perspective view of a second embodiment of an expandable body device for the gastric cavity according to the present invention.
Figure 5:
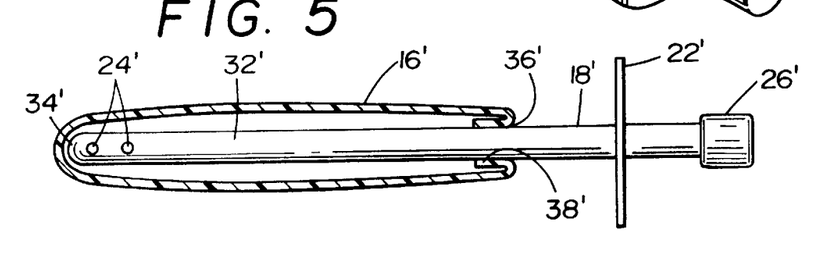
FIG. 5 shows a longitudinal partial cross-sectional view of the expandable body device shown in FIG. 4.
Figure 6:
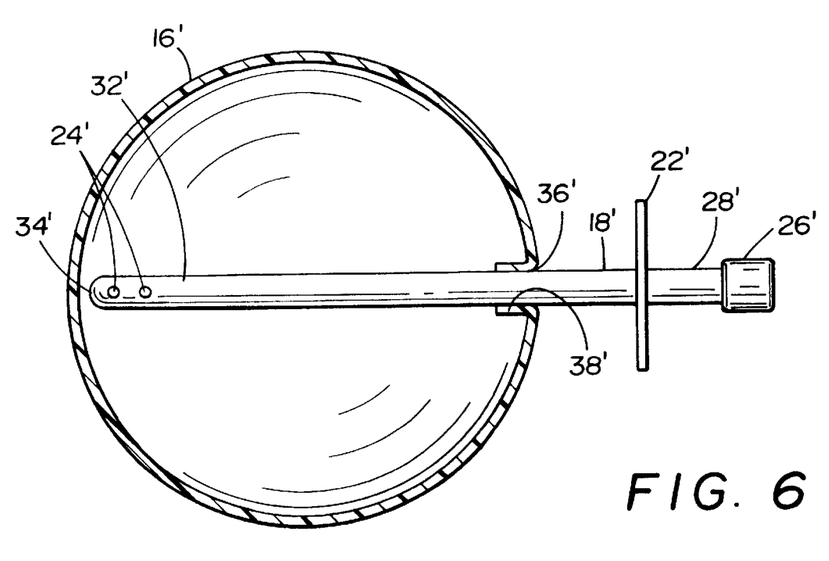
FIG. 6 shows a longitudinal partial cross-sectional view of the expandable body device shown in FIG. 3 while the expandable body is in an expanded configuration.

A second embodiment of a expandable body device for the gastric cavity is shown in FIGS. 4–6. The fillant delivery tube 18' of the embodiment shown in FIGS. 4–6 is, like the fillant delivery tube of the device shown in the first embodiment, a cylindrical and substantially rigid tube having a linear centerline and a uniform cross-section. The centerline of fillant delivery tube 18' may vary according to the present invention. For example, the centerline of a fillant delivery tube according to the present invention may define a curvilinear path, such as a single plane S-like path, or, as another example, a substantially corkscrew-like path. Further, the longitudinal or transverse cross-sectional profile of fillant delivery tube may vary. For example, fillant delivery tube 18' may have a longitudinal cross-sectional profile which expands or tapers along the centerline of fillant delivery tube 18'. As another example, the transverse cross-sectional profile of fillant delivery tube 18' may have a non-circular shape such as eye-shaped or polygon-shaped.

Base portion 28', extending portion 32', and tip portion 34' of fillant delivery tube 18' are integral, as shown in FIGS. 4–6. In other embodiments (not shown) base portion 28' may be configured to releasably connect to extending portion 32' so that a user of the device is able to select a combination of base portion 28' and extending portion 32' appropriate for a particular individual. That is, for some individuals it may be desirous to have a somewhat flexible base portion connected to a rigid extending portion. As another example, for some individuals it may be desirous to connect an extending portion having a relatively large longitudinal dimension to a base portion having a relatively small longitudinal dimension.

A detachable connection between base portion 28 and extending portion 32 may be established by including a proximal internally threaded surface on extending portion 32 which threadedly engages a corresponding distal externally threaded surface of base portion 28'. Other connections could also be utilized, for example, a press-fit or an interference fit.

A detachable connection between base portion 28' and extending portion 32' may be dynamic. For example, extending portion 32' may be configured to rotate relative to base portion 28' Alternatively, extending portion 32' may be configured to slide axially relative to base portion 28'.

Fillant delivery tube 18' shown in FIG. 4 also includes a closed and substantially rounded distal tip portion 34' provided with two (2) pairs of diametrically opposed passages 24' through which a fillant may be delivered to expandable body 16'.

The expandable body 16' of the embodiment shown in FIGS. 4–6 is sealedly connected to fillant delivery tube 18' at sealed connection 36'. Preferably, sealed connection 36' is provided chemically, as shown in FIGS. 4–6, by an adhesive disposed between expandable body 16' and fillant delivery tube 18', or for example, by sonic welding. However, sealed connection 36' may be provided mechanically, for example by a band, a sleeve, a length of cord, or some other form of mechanical constricting device (not shown) having a profile which would not impede passage of the device through the gastric fistula. As another example, sealed connection 36' may be provided by configuring a base portion of fillant delivery tube 18' to engage an extending portion with a portion of expandable body 16' secured therebetween.

Note from FIGS. 5 and 6 that expandable body 16' is partially inverted such that the outer surface of integral band portion 38' is in contact with the outer surface of fillant delivery tube 18' at sealed connection 36' This partial inversion of expandable body 16' allows for a large amount of surface area of fillant delivery tube 18' to be exposed between anchor 22' and expandable body 16'.

To prevent potentially injurious rupturing of the expandable body, the sealed connection between the expandable body and the fillant delivery tube may be configured to release at or prior to the internal pressure of the device reaching a predetermined maximum.

The expandable body 16' of device 14' shown in FIGS. 4–6 is an elastic structure preferably having predetermined memory characteristics i.e. configured to expand to a predetermined shape and to resume original shape upon evacuation of fillant therefrom. Porous or selectively permeable materials which allow passage of a fillant in a controlled manner into the gastric cavity or materials impregnated or saturated with a biocompatible lubricant may also be used to construct expandable body 16'.

In FIGS. 4–5, the expandable body 16' of device 14' is shown in a substantially non-expanded configuration. While in a non-expanded configuration, expandable body 16' forms a single layer of material which is substantially congruent with the surface of tip portion 34'.

In some embodiments (not shown), it is preferable to sealedly connect expandable body 16' to fillant delivery tube 18' such that the tip portion 34' of fillant delivery tube 18' is in contact with the inner surface of expandable body 18'. In embodiments where tip portion 34' contacts the inner surface of expandable body 18', expandable body 18' may be slightly taut while in a non-expanded configuration so as to further ensure the uniformity of expandable body 16' around tip portion 34'.

FIG. 6 shows the expandable body 16' of device 14' in an expanded configuration. Note from FIG. 3 that expandable body 16' is preferably configured to expand into a substantially spherical shape.

Device 14' shown in FIGS. 4–6 also includes an annular disc-shaped plastic anchor 22' mounted proximally on fillant delivery member 18' for controlling the depth to which device 14' is inserted through a gastric fistula. Anchor 22' is preferably of sufficient diameter to provide a surface against which a force may be applied by the fingers of the user for pushing the device 14' through a gastric fistula. The shape and texture of anchor 22' may vary, for example, anchor 22' may be concave or convex. As another example, anchor 22' may be knurled, ridged or bumped. Anchors 22' may be configured for interchangeability such that an appropriate anchor 22' for any individual may be selected. For example, in embodiments where base portion 28' and extending portion 32' are separable and attachable, anchor 22' may be configured to mount therebetween for easy replacement.

The embodiment shown in FIGS. 4–6 also includes a valve 26' for allowing fillant to be introduced and released from the fillant delivery tube 18'. Valve 26' may include a pressure regulator such that when the pressure within device 14 reaches or exceeds a predetermined maximum, valve 26' opens to release the excess pressure from the device 14'.

Figure 7:
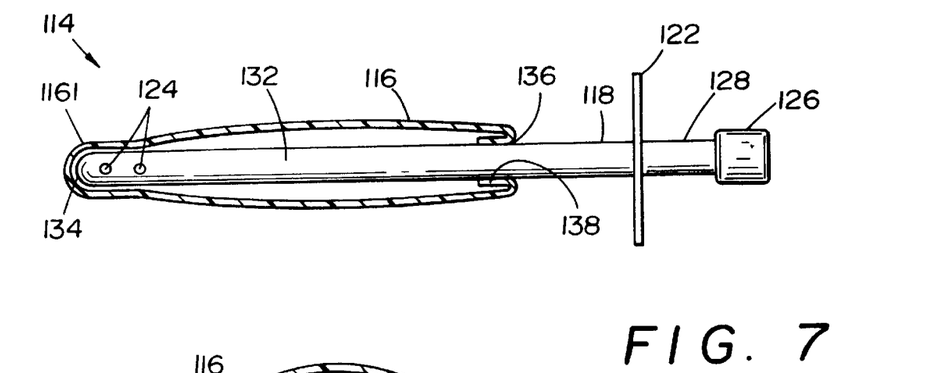
FIG. 7 shows a longitudinal partial cross-sectional view of a third embodiment of an expandable body device according to the present invention.
Figure 8:
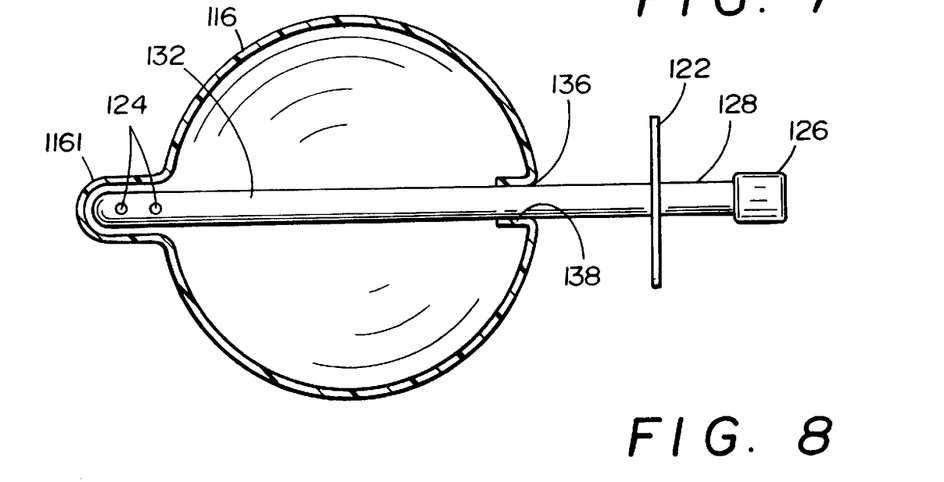
FIG. 8 shows a longitudinal partial cross-sectional view of the expandable body device shown in FIG. 7 while the expandable body is in an expanded configuration.

A third embodiment of a device 114 according to the present invention is shown in FIGS. 7 and 8. Device 114 includes an expandable body 116 having a nose portion 1161 of a relatively greater elasticity (i.e. less elastic) than the remaining portion of expandable body 116. Thus, note that when a fillant is pumped into expandable body 116 as shown in FIG. 5, the nose portion 1161 does not expand to the same extent as the remaining portion of expandable body 116. Because nose portion 1161 remains substantially and closely congruent with tip portion 134 while expandable body 116 is in an expanded configuration, the relative movement between expandable body 116 and fillant delivery tube 118 is limited. To even further decrease relative movement between expandable body 116 and fillant delivery tube 118, tip portion 134 may be attached to the interior surface of expandable body 116 at nose portion 1161, however, this may necessitate the relocation of passages 124 in extending portion 132 further proximally on fillant delivery tube 18.

Figure 9:
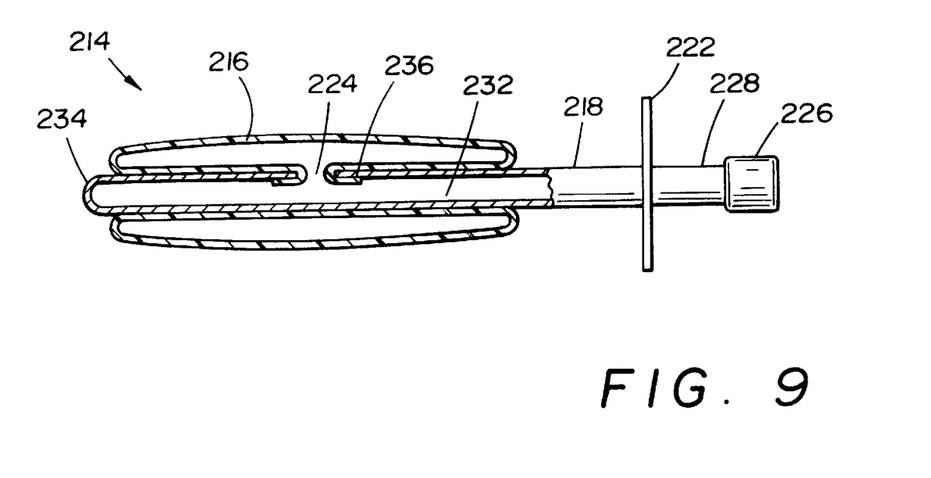
FIG. 9 shows a longitudinal partial cross-sectional view of a fourth embodiment of an expandable body device according to the present invention.
Figure 10:
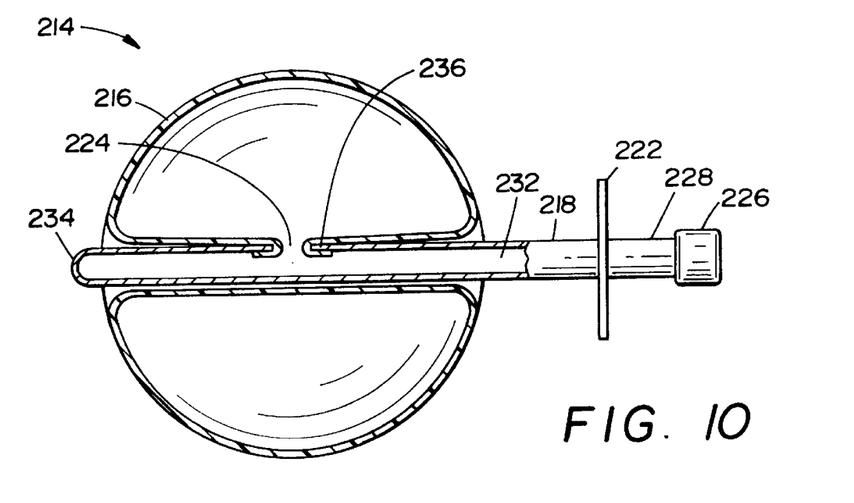
FIG. 10 shows a longitudinal partial cross-sectional view of the expandable body device shown in FIG. 9 while the expandable body is in an expanded configuration.
Figure 11:
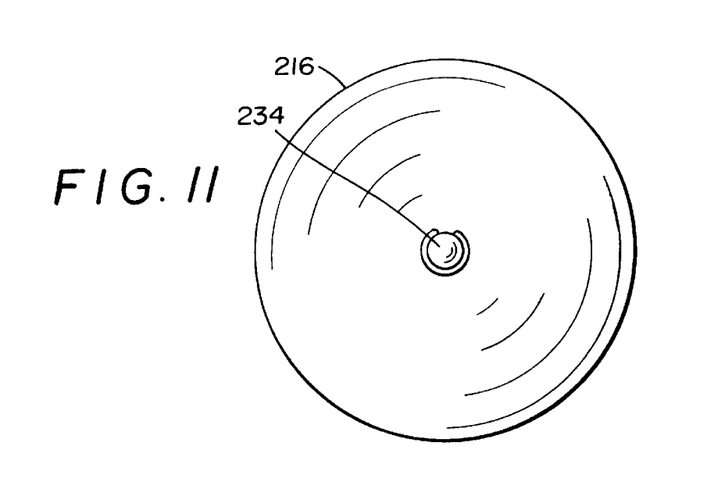
FIG. 11 shows an end view of the expandable body device shown in FIG. 10.

A fourth embodiment of a device 214 according to the present invention is shown in FIGS. 9–11. Device 214 includes a substantially annular expandable body 216 through which the extending portion 232 of fillant delivery tube 218 passes. Note that this configuration prevents relative pivoting movement between expandable body 216 and fillant delivery tube 218. Relative rotational movement about the coincidental longitudinal axis of fillant delivery tube 218 and expandable body 216 is prevented by sealed connection 236.

Figure 12:
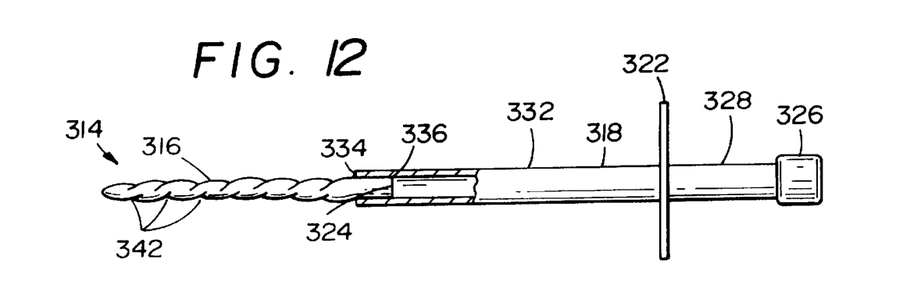
FIG. 12 shows a longitudinal partial cross-sectional view of a fifth embodiment of an expandable body device according to the present invention.
Figure 13:
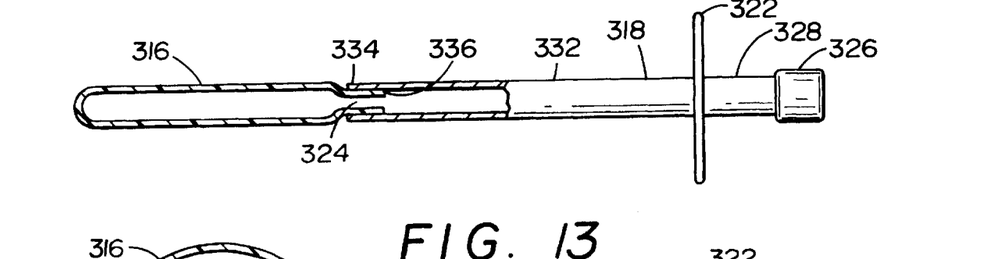
FIG. 13 shows a longitudinal partial cross-sectional view of the expandable body device shown in FIG. 12 while the expandable body is in a partially expanded configuration.
Figure 14:
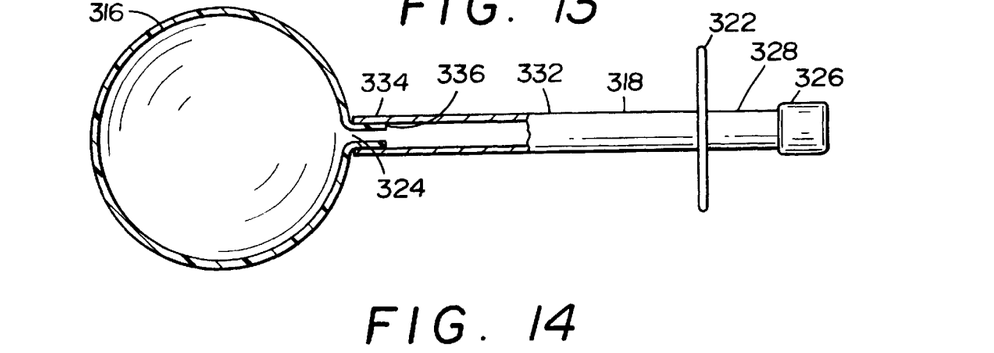
FIG. 14 shows a longitudinal partial cross-sectional view of the expandable body device shown in FIG. 12 while the expandable body is in a fully expanded configuration.

A fifth embodiment of a device for insertion into the gastric cavity for the treatment of obesity is shown in FIGS. 12–14. Device 314 includes an expandable body 316 which is mounted within and extends distally from a passage 324 at the tip portion 334 of fillant delivery tube extending portion 332. The expandable body 316 of device 314 is made of an elastic material having predetermined memory characteristics, in particular, expandable body 216 assumes the spiral-shaped configuration shown in FIG. 12 while in a non-expanded configuration. Note the relatively small transverse and longitudinal cross-sectional profile of expandable body 316 in FIG. 12.

As expandable body 316 expands with the delivery of fillant from passage 324, each turn 342 of expandable body 316 is forced from the spiral-shaped configuration shown in FIG. 12 into the substantially cylindrical configuration shown in FIG. 13. As more fillant is delivered to expandable body 316, the expandable body 316 of device 314 expands to the substantially spherical configuration shown in FIG. 14.

Preferably, expandable body 316 is configured to return to the spiral-shaped 5 configuration shown in FIG. 14 simply by the release of fillant therefrom. However, with the additional step of providing a vacuum to the expandable body 316 via the fillant delivery tube 318 and valve 326, a more rapid and complete removal of fillant from expandable body 316 may be effected. Note that the application of a vacuum to the expandable body 316 would also substantially decrease the flexibility of expandable body 316 thus further easing introduction of device 314 to, and removal of device 314 from, the gastric cavity.

Figure 15:
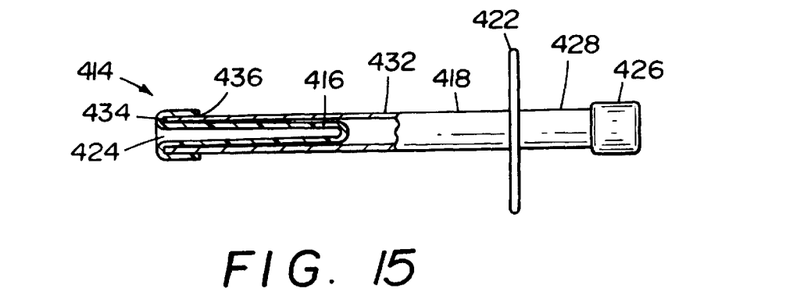
FIG. 15 shows a longitudinal partial cross-sectional view of a sixth embodiment of an expandable body device according to the present invention.
Figure 16:
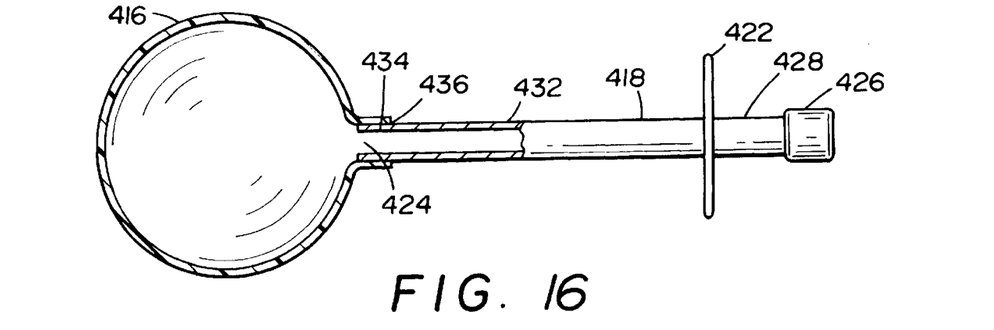
FIG. 16 shows a longitudinal partial cross-sectional view of the expandable body device shown in FIG. 15 while the expandable body is in a fuilly expanded configuration.

A sixth embodiment of a device 414 according to the present invention is shown in FIGS. 15–16. Device 416 includes a passage 424 in the tip portion 434 of the fillant delivery tube 418. Expandable body 416 is mounted to the outer surface of fillant delivery tube 418 at tip portion 434. Note from FIG. 15 that, while in a non-expanded configuration, expandable body 416 is stored within the fillant delivery tube 418, thus minimizing the transverse cross-sectional profile of device 414. Once within the gastric cavity, expandable body 416 is caused to expand, as shown in FIG. 16, by the delivery of fillant from fillant delivery tube 418. Preferably, expandable body 418 is returned to the configuration shown in FIG. 15 by the creation of a vacuum condition within the fillant delivery tube 418.

Figure 17:
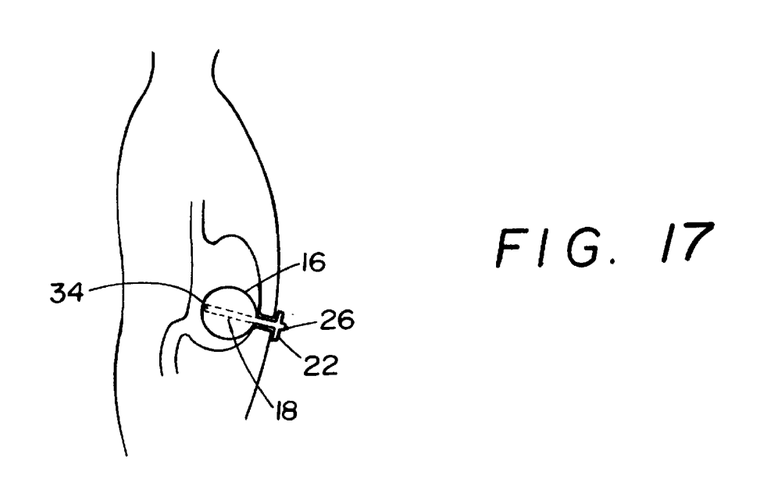
FIG. 17 shows a schematic view of the expandable body device of the present invention introduced to the gastric cavity of an obese individual.
Figure 18:
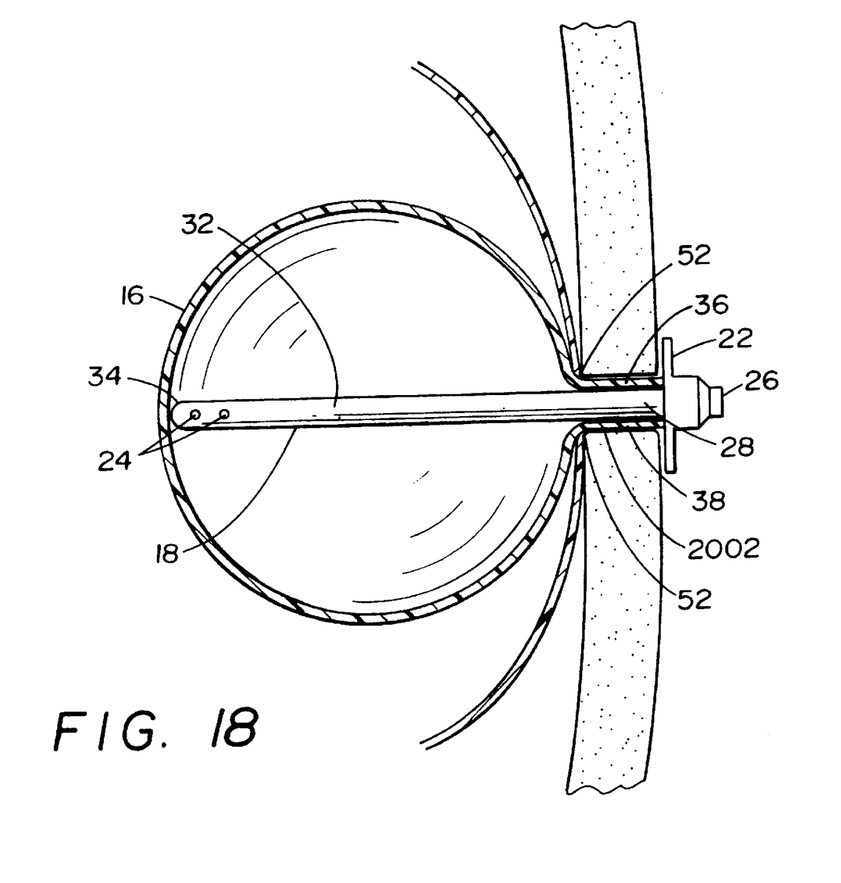
FIG. 18 shows a partial longitudinal cross-sectional view of the expandable body device within the gastric cavity of an individual.

A preferred method of inserting the device of the present invention into the gastric cavity, and more particularly, a preferred method of inserting the device into the gastric cavity for the treatment of obesity will now be described. In FIGS. 17 and 18, device 14 shown in FIGS. 1–3 is shown inserted into the gastric cavity of a human 10 according to a preferred method of the present invention.

In the first step of the method, a gastro-cutaneous fistula 2002 is established in the obese individual via a percutaneous endoscopic gastrostomy, a procedure known to persons skilled in the art. The cross-sectional profile of the fistula tract is configured to correspond with the cross-sectional profile of the device along the expandable body. Preferably, the fistula tract is allowed to mature (i.e. form scar tissue), typically, over a period of from 1–2 weeks.

In the second step of the method, the device 14 is brought into proximity of the fistula tract and a bio-compatible lubricant is applied to the device and/or to the fistula tract. The expandable body 16 along tip portion 34 of fillant delivery tube 18 is placed at the entrance of the fistula tract and passed through the fistula 2002 by the application of a gentle force at the base portion of the fillant delivery tube 18. The proximal surface of anchor 22 provides a convenient surface against which such a force may be applied. The device is preferably configured so that complete insertion is indicated when the anchor 22 contacts the abdominal wall.

Since the relatively soft material of expandable body 16 covers tip portion 34 and at least a substantial fraction of extending portion 32, a gentle surface is provided for contacting the tissue of fistula 2002 during insertion of the device 14 into the gastric cavity. Further, the soft material of expandable body 16 in combination with the rounded tip portion 34 may be used to gently and safely stretch the elastic tissue of the fistula 2002. Thus, the present invention allows for the use of a fistula 2002 having a transverse cross-sectional profile which is approximately the same size or even somewhat smaller than the largest transverse cross-sectional profile of the device 14 distal of anchor 22.

In the third step, a biocompatible fillant, preferably, saline solution, is introduced to the device. Preferably, a graduated syringe (not shown) is loaded with an appropriate amount of biocompatible fillant, typically 10–500 ml. The syringe is then sealedly engaged with the valve 26 on the proximal end of the fillant delivery tube 18. The syringe plunger is advanced and fillant passes through the fillant delivery tube 18 and into the expandable body 16 which is thereby caused to expand within the gastric cavity. Once appropriate expansion size is reached, the tip of the syringe is removed from the valve 26 which is preferably configured to close upon withdrawal of the syringe.

Alternatively, a hose (not shown) may be connected between a fillant supply pump (not shown) and valve 26 on the preferred embodiment of device 14. Valve 26 is opened and a preferably biocompatible fillant in liquid, gas, or gel form is pumped through valve 26 and into fillant delivery tube 18. The fillant exits passages 24 in fillant delivery tube 18 and enters expandable body 16 causing the expandable body 16 to expand within the gastric cavity. The fourth step is completed upon closure of the valve 26 and removal of the hose 52 therefrom.

The size of the of the expandable body 16 is preferably configured so that when appropriate expansion size is reached, the expandable body 16 occupies a substantial fraction of the total volume of the gastric cavity of the person in whose gastric cavity the device has been inserted but remains substantially free of contact with the gastric wall. The loss in stomach capacity available for food enables the individual to feel satiated or "full" after consuming a relatively small portion of food.

Note from FIG. 18 that as expandable body 16 expands, a proximal portion of expandable body 16 contacts the surface of the gastric entrance of the fistula, indicated as 52. The contact between the outer surface of expandable body 16 and the fistula entrance serves to prevent the escape of gastric juices from the gastric cavity and to maintain the device 14 in a fixed position relative to the person in whose gastric cavity the device has been introduced. Thus, the individual may remain active while the expandable body 16 is in an expanded configuration within the gastric cavity. It is also important to note that, when the device is fully inserted, the distance from the surface of the abdomen proximal of the anchor 22 to the valve 26 is relatively small, preferably less than 3 centimeters, thus preventing others from easily noticing the device during use.

In the fourth step, a period of time is allowed to elapse, preferably 3 to 6 months, and the syringe is again engaged with the valve 26. The syringe is operated to create a vacuum condition in the device 14, thereby causing fillant to flow from the device 14 into the syringe until the expandable body 16 is returned to a non-expanded configuration. After the expandable body is returned to a non-expanded configuration, the device 14 may be, for example, removed from the gastric cavity and replaced with another device 14 having an expandable body with a different volume.

Alternatively, a hose may be connected to the valve 26. Upon opening of the valve, the compressive force created by the elastic material of expandable body 16 causes the fillant to flow from the expandable body 16 into the fillant delivery tube 18 and out of the device 14. The device 14 may then be re-filled with fillant or removed from the gastric cavity.

During withdrawal, the fistula may contact the outer surface of the expandable body 16 which in turn causes the expandable body to contact the extending portion of fillant delivery tube 18. The compression of the expandable body causes any remaining fillant to be pushed into passages 24. Since the passages are located at the tip portion 34 of the fillant delivery tube 18, they are not blocked due to the contact of the expandable with the extending portion 32 of the fillant delivery tube 18.

Thus, the present invention is particularly suitable for use as part of a therapy for weight loss in morbidly obese patients. It is important to recognize however, that the present invention may be introduced to the gastric cavity for other purposes. For example, the present invention may be introduced to the gastric cavity for the treatment of hypothermia. In such a use, the device may be inserted as described above, however, a fillant having a temperature higher than normal body temperature may be delivered to expandable body for supplying heat energy internally of the hypothermic individual.

Alternatively, in embodiments where an expandable body made of a porous or selectively permeable material is used, the present invention may be used to deliver a drug, for example, by diffusion through the expandable body, to the individual in whose gastric cavity the device has been introduced.

Thus, the present invention has many uses and configurations, and while certain representative embodiments and details have been described for the purpose of illustrating the invention, it will be apparent to those skilled in the art that various changes and modifications may be made therein without departing from the spirit or scope of the invention.

What is claimed is:

1. A surgical device for positioning in the gastric cavity for the treatment of obesity, said device comprising:
    a substantially rigid fillant delivery tube, for delivering fillant to a separate elastic expandable body including a base portion, an extending portion, and a tip portion, said delivery tube sealedly connected to said expandable body and configured to translate said separate expandable body through a percutaneous gastric fistula and to extend a substantial distance into the gastric cavity for preventing excessive pivoting of said expandable body within the gastric cavity;
    said separate elastic expandable body surrounding said delivery tube and directly sealedly connected thereto;
    said separate elastic expandable body being configured to expand to a substantially spherical configuration within the gastric cavity and to sealedly contact the perimeter of the gastric opening of said fistula;
    an anchor attached to said base portion of said fillant delivery tube; and,
    a valve attached to said base portion of said fillant delivery tube.

2. A device according to claim 1, wherein said tip portion of said extending portion is closed and rounded and said fillant delivery tube includes at least one passage for allowing said fillant to be delivered to said expandable body.

3. A device according to claim 1, wherein said tip portion and extending portion extend into said expandable body.

4. A device according to claim 1, wherein said expandable body includes an integral band portion attached to said fillant delivery tube.

5. A device according to claim 1, wherein said expandable body is configured to expand to a specific shape.

6. A device according to claim 5, wherein said expandable body is configured to expand to a substantially spherical shape.

7. A device according to claim 5, wherein said expandable body is configured to maintain a specific shape while in a non-expanded configuration.

8. A device according to claim 7, wherein said expandable body is sealedly connected to and extends distally from said tip portion and is configured to maintain a substantially spiral shape while in a non-expanded configuration.

9. A device according to claim 1, wherein said expandable body is stored within said fillant delivery tube while in a non-expanded configuration.

10. A device according to claim 1, wherein said expandable body includes a nose portion.

11. A device according to claim 10, wherein said nose portion maintains a predefined shape during expansion and while expanded.

12. A device according to claim 1, wherein said tip portion of said extending portion is connected to an inner surface of said expandable body.

13. A method of treating obesity comprising the steps of:
    performing a percutaneous endoscopic gastrostomy to establish a gastrocutaneous fistula;
    pushing an expandable body through said fistula into said gastric cavity with a rigid fillant delivery tube to which said expandable body is sealedly connected, said rigid fillant delivery tube including a base portion, an extending portion, a tip portion, and an anchor attached to said base portion;
    delivering a fillant through a valve connected to said fillant delivery tube such that said fillant flows into said fillant delivery tube and said expandable body to cause said expandable body to expand within said gastric cavity; and,
    delivering said fillant through said valve out of said fillant delivery tube and said expandable body to cause said expandable body to return to a non-expanded configuration; and,
    removing said fillant delivery tube and said expandable body from said fistula.

14. A device according to claim 4, wherein said integral band portion is inverted such that the outer surface of said integral band portion is in contact with the outer surface of fillant delivery tube and sealedly connected thereto.

15. A device according to claim 1, wherein said valve and said anchor are integral.

16. A device according to claim 15, wherein said integral valve and anchor are press fit onto said fillant delivery tube.

17. A device according to claim 16, wherein said integral band portion of said expandable body is sealedly connected to said rigid fillant delivery tube between said integral valve and anchor and said rigid fillant delivery tube.

* * * * *